US008741344B1

(12) United States Patent
Dumbre et al.

(10) Patent No.: US 8,741,344 B1
(45) Date of Patent: Jun. 3, 2014

(54) DISPERSIBLE TABLET

(71) Applicant: Azanta A/S, Hellerup (DK)

(72) Inventors: Nilesh Tanhaji Dumbre, Pune (IN); Mahesh Mohanrao Bhadgale, Pune (IN); Vardhaman Chandrakant Bafna, Pune (IN)

(73) Assignee: Azanta A/S, Hellerup (DK)

( * ) Notice: Subject to any disclaimer, the term of this patent is extended or adjusted under 35 U.S.C. 154(b) by 0 days.

(21) Appl. No.: 14/193,761

(22) Filed: Feb. 28, 2014

Related U.S. Application Data

(62) Division of application No. 13/680,216, filed on Nov. 19, 2012, now Pat. No. 8,703,188.

(51) Int. Cl.
*A61K 9/20* (2006.01)

(52) U.S. Cl.
USPC ....... 424/464; 118/715; 514/235.8; 514/20.5; 424/489

(58) Field of Classification Search
None
See application file for complete search history.

(56) References Cited

U.S. PATENT DOCUMENTS

| | | | |
|---|---|---|---|
| 3,483,212 | A | 12/1969 | Miller et al. |
| 4,218,449 | A | 8/1980 | Wyburn-Mason |
| 4,371,540 | A | 2/1983 | Lee et al. |
| 4,462,992 | A | 7/1984 | Agrawal et al. |
| 2002/0012658 | A1 | 1/2002 | Williams |
| 2006/0078614 | A1 | 4/2006 | Venkatesh |
| 2010/0322939 | A1 | 12/2010 | Overgaard |
| 2011/0135712 | A1 | 6/2011 | McChesney et al. |

FOREIGN PATENT DOCUMENTS

| | | | |
|---|---|---|---|
| WO | WO 2008/154927 | A1 | 12/2008 |
| WO | WO 2012/146259 | A1 | 11/2012 |

OTHER PUBLICATIONS

Adams et al. "Electron-Affinic Sensitization," Radiation Research, vol. 67, pp. 9-20 (1976).
Bourhis et al. "Hyperfractionated or accelerated radiotherapy in head and neck cancer: a meta-analysis," The Lancet, vol. 368: pp. 843-854 (2006).
Brizel et al. "Tumor Hypoxia Adversely Affects the Prognosis of Carcinoma of the Head and Neck," Int J. Radiation Oncology Biol. Phys, vol. 38: pp. 285-289, (1997).
Cantelli-Forti et al. "Mutagenicity of a Series of 25 Nitroimidazoles and Two Nitrothiazoles in *Salmonella typhimurium*," Teratogenesis, Carcinogenesis, and Mutagenesis, vol. 3 pp. 51-63, (1983).
Conley "Treatment of Advanced Head and Neck Cancer: What Lessons Have We Learned?," Journal of Clinical Oncology, vol. 24 No. 7, pp. 1023-1025, (2006).
Cottrill et al. "Pilot Study of Nimorazole as a Hypoxic-cell Sensitizer With the "Chart" Regimen in Head and Neck Cancer," Int. J. Radiation Oncology Biol. Phys, vol. 42 No. 4, pp. 807-810, (1998).
Duvvuri "In Brief," Current Problems in Surgery, vol. 46, pp. 114-117, (2009).
Fakhry et al. "Clinical Implications of Human Papillomavirus in Head and Neck Cancers," Journal of Clinical Oncology, vol. 24 No. 17, pp. 2606-2611, (2006).
Grau et al. "Effect of cancer chemotherapy on the hypoxic fraction of a solid tumor measured using a local tumor control assay," Radiotherapy and Oncology, vol. 13 No. 4, pp. 301-309, (1988).
Grau et al. "Radiotherapy with or without mitomycine c in the treatment of locally advanced head and neck cancer: results of the IAEA mulitcentre randomised trial," Radiotherapy and Oncology, vol. 67 No. 1, pp. 17-26 (2003).
Gritz et al. "First Year After Head and Neck Cancer: Quality of Life," Journal of Clinical Oncology vol. 17 No. 1, pp. 352-360, (1999).
Hashibe et al. "Alcohol Drinking in Never Users of Tobacco, Cigarette Smoking in Never Drinkers, and the Risk of Head and Neck Cancer: Pooled Analysis in the International Head and Neck Cancer Epidemiology Consortium," JNCI, vol. 99 No. 10, pp. 777-789. (2007).
Henk et al. "Treatment of head and neck cancer with CHART and nimoraizole: phase II study," Radiotherapy and Oncology, vol. 66, pp. 65-70, (2003).
Anonymous "Cancer in Scotland," NHS National Services Scotland, 19 pages (2009).
Horsman et al. "Tumor Radiosensitizers—Current Status of Development of Various Approaches: Report of an International Atomic Energy Agency Meeting," Int. J. Radiation Oncology Biol. Phys, vol. 64 No. 2, pp. 551-561, (2006).
Kaanders et al. "Clinical Studies of Hypoxia Modification in Radiotherapy," Seminars in Radiation Oncology, vol. 14 No. 3, pp. 233-240, (2004).
Lefebvre "Current clinical outcomes demand new treatment options for SCCHN," Annals of Oncology. vol. 16 (6), pp. vi7-vi12, (2005).
McKaig et al. "Human Papillomavirus and Head and Neck Cancer: Epidemiology and Molecular Biology," Head & Neck, vol. 20, pp. 250-265, May 1998.
Minn et al. "Effect of Nitroimidazole Sensitizers on In Vitro Glycolytic Metabolism of Hypoxic Squamous Cell Carcinoma," Acta Oncologica, vol. 39 No. 2, pp. 199-205, (2000).
Nordsmark et al. "Pretreatment oxygenation predicts radiation response in advanced squamous cell carcinoma of the head and neck," Radiotherapy and Oncology, vol. 41, pp. 31-39, (1996).
Nordsmark et al. "A confirmatory prognostic study on oxygenation status and loco-regional control in advanced head and neck squamous cell carcinoma treated by radiation therapy," Radiotherapy and Oncology, vol. 57, pp. 39-43, (2000).
Nordmark et al. "Prognostic value of tumor oxygenation in 397 head and neck tumors after primary radiation therapy. An international multi-center study," Radiotherapy and Oncology, vol. 77, pp. 18-24, (2005).

(Continued)

*Primary Examiner* — Hasan Ahmed
(74) *Attorney, Agent, or Firm* — McLane, Graf, Raulerson & Middleton, PA

(57) ABSTRACT

The present invention relates to a tablet comprising Nimorazole. In particular, the invention concerns a pharmaceutical composition or a tablet comprising Nimorazole or a pharmaceutically acceptable salt, for dispersion in water and administration via a tube to a patient with swallowing difficulties.

21 Claims, No Drawings

(56) References Cited

OTHER PUBLICATIONS

Overgaard "Hypoxic modification of radiotherapy in squamous cell carcinoma of the head and neck—A systematic review and meta-analysis," Radiotherapy and Oncology, vol. 100, pp. 22-32, (2011).
Overgaard et al. "A Comparative Investigation of Nimorazole and Misonidazole as Hypoxic Radiosensitizers in a C3H Mammary Carcinoma In Vivo," Br. J. Cancer, vol. 46. pp. 904-911, (1982).
Overgaard et al. "Studies of the pharmacokinetic properties of nimorazole," Br. J. Cancer, vol. 48, pp. 27-34, (1983).
Overgaard et al. "Misonidazole Combined with Split-Course Radiotherapy in the Treatment of Invasive Carcinoma of Larynx and Pharynx: Report From the Dahanca 2 Study," Int. J. Radiation Oncology Biol. Phys, vol. 16, pp. 1065-1068, (1989).
Overgaard "Clinical Evaluation of Nitroimidazoles as Modifiers of Hypoxia in Solid Tumors," Oncology Research, vol. 6 No. 10-11, pp. 509-518, (1994).
Overgaard et al. "Modification of Hypoxia-induced Radioresistance in Tumors by the Use of Oxygen and Sensitizers," Seminars in Radiation Oncology, vol. 6 No. 1, pp. 10-21, (1996).
Overgaard et al. "A randomized double-blind phase III study of nimorazole as a hypoxic radiosensitizer of primary radiotherapy in supraglottic larynx and pharynx carcinoma. Results of the Danish Head and Neck Cancer Study (DAHANCA) Protocol 5-85," Radiotherapy and Oncology, vol. 46 No. 2, pp. 135-146, (1998).
Overgaard et al. "A randomized trial with 1485 patients evaluating the importance of accelerated versus conventional fractionated radiotherapy in squamous cell carcinoma of the head and neck. Final results of the DAHANCA 6&7 study," European Journal of Cancer supplements, vol. 1 No. 5, pp. 318, (2003).
Overgaard et al. "Five compared with six fractions per week of conventional radiotherapy of squamous-cell carcinoma of head and neck: DAHANCA 6&7 randomised controlled trial," The Lancet, vol. 362, pp. 933-940, (2003).
Overgaard "Hypoxic Radiosensitization: Adored and Ignored," Journal of Clinical Oncology, vol. 25 No. 26, pp. 4066-4074, (2007).
Raether et al. "Nitroheterocyclic drugs with broad spectrum activity," Parasitol Res., vol. 90, pp. 19-39, (2003).
Rischin et al. "Prognostic Significance of [18F]-Misonidazole Positron Emission Tomography-Detected Tumor Hypoxia in Patients With Advanced Head and Neck Cancer Randomly Assigned to Chemoradiation With or Without Tirapazaminer: A Substudy of Trans-Tasman Radiation Oncology Group Study 98.02," Journal of Clinical Oncology, vol. 24 No. 13, pp. 2098-2104, (2006).
Santiago et al. "Effect of cetuximab and fractionated irradiation on tumour micro-environment," Radiotherapy and Oncology, vol. 97 No. 2, pp. 322-329, (2010).
Saunders et al. "Clinical results of hypoxic cell radiosensitisation from hyperbaric oxygen to accelerated radiotherapy, carbogen and nicotinamide," British Journal of Cancer, vol. 74, pp. 271-278, (1996).
Scott et al. "Laryngeal Cancer in Scotland. 1960-1994: Trends in Incidence, Geographical Distribution and Survival," Health Bulletin, vol. 56 No. 4, pp. 749-757, (1998).
Seiwert et al. "The chemoradiation paradigm in head and neck cancer," Nature Clinical Practice Oncology, vol. 4 No. 3, pp. 156-171, (2007).
Timothy et al. "A Phase I Clinical Study of Nimorazole as a Hypoxic Radiosensitizer," Int. J. Radiation Oncology Biol. Phys, vol. 10 No. 9, pp. 1765-1768, (1984).
Voogd et al. "The Mutagenic Action of Nitroimidazoles I. Metronidazoles, Nimorazole Dimetridazole and Ronidazole," Mutation Research, vol. 26 No. 6, pp. 403-490, (1974).
Wardman "Chemical Radiosensitizers for Use in Radiotherapy," Clinical Oncology, vol. 19 No. 6, pp, 397-417, (2007).
Withers et al. "The Hazard of Accelerated Tumor Clonogen Repopulation During Radiotherapy," Acta Oncologica, vol. 27 No. 2, pp. 131-146, (1988).
Chawla et al. "Temporal assessment of quality of life of head and neck cancer patients receiving radical radiotherapy," Quality of Life Research, vol. 8, pp. 73-78, (1999).
Colevas "Chemotherapy Options for Patients With Metastatic or Recurrent Squamous Cell Carcinoma of the Head and Neck" Journal of Clinical Oncology, vol. 24 No. 17, pp. 2644-2652, (2006).
Corvo "Evidence-based radiation oncology in head and neck squamous cell carcinoma," Radiotherapy and Oncology, vol. 85, pp. 156-170, (2007).
Curado et al. "Recent changes in the epidemiology of head and neck cancer," vol. 21, pp. 194-200, (2009).
Anonymous "Stakeholder Opinions: Head and Neck Cancer," Datamonitor, www.datamonitor.com, 96 pages, (2007).
Matzinger et al. "Radiochemotherapy in Locally Advanced Squamous Cell Carcinomas of the Head and Neck," Clinical Oncology, vol. 21 No. 7, pp. 1-7, (2009).
Stockton, Cancer in Scotland: Sustaining Change,: www.scotland.gov.uk, 18 pages, (2004).
Anonymous "Prevalence of rare diseases: Bibliographic data," Orphanet Report Series. Rare Diseases collection, No. 1, 28 pages, (2008).
Overgaard et al. "Nimorazole as a hypoxic radiosensitizer in the treatment of supraglottic larynx and pharynx carcinoma. First report from the Danish Head and Neck Cancer Study (DAHANCA) protocol 5-85," Radiotherapy and Oncology, vol. 20, pp. 141-149, (1991).
Parkin et al. "Global Cancer Statistics, 2002," CA A Cancer Journal for Clinicians, Vol. 55 No. 2, pp. 74-108, (2005).
Pinto et al. "Chemotherapy for Recurrent and Metastatic Head and Neck Cancer," Hematology/Oncology Clinic's of North America, vol. 5 No. 4, pp. 667-686, (1991).
Pivot "ESMO Minimum Clinical Recommendations for diagnosis, treatment and follow-up of squamous cell carcinoma of the head and neck," Annals of Oncology, vol. 14 No. 7, pp. 1014-1015, (2003).
Sant et al. "EUROCARE-3: survival of cancer patients diagnosed 1990-94—results and commentary," Annals of Oncology, vol. 14 No. 5, pp. 61-118, (2003).
Sant et al. "EUROCARE-4. Survival of cancer patients diagnosed in 1995-1999. Results and commentary," European Journal of Cancer, vol. 45, pp. 931-991, (2009).
Juror et al. "Diagnosis and management of head and neck cancer. A national clinical guideline," SIGN publication, No. 90, 29 pages, (2006).
Toustrup et al. "Development of a Hypoxia Gene Expression Classifier with Predictive Impact for Hypoxic Modification of Radiotherapy in Head and Neck Cancer," Cancer Research, vol. 71 No. 17, pp. 5923-5931, (2011).
Toustrup et al. "Gene Expression Classifier Predicts for Hypoxic Modification of Radiotherapy with Nimorazole in Squamous Cell Carcinomas of the Head and Neck," Radiotherapy and Oncology, vol. 102, pp. 122-129, (2012).
Ratnaparkhi et al. "Formulation and In-Vitro Characterization of Nimorazole Mouth Dissolving Tablets," Research Journal of Pharmaceutical, Biological and Chemical Sciences, vol. 3 No. 3, pp. 303-308, (2012).
Anonymous "EuropeanMedicines Agency—Human medicines—Rare disease (orphan) designations," 1 page.
Anonymous "Feeding tube," Wikipedia, en.wikipedia.org , 5 pages (2012).
Bowman, "Administration of drugs to patients with swallowing difficulties," Journal of the Malta College of Pharmacy Practice, vol. 12, pp. 42-45, (2007).
Anonymous "Tablets" PH Eur Dispersible tablet, 5 pages, (2008).
Anonymous "Naxogin tablets 500mg #6," www.pharmoutlet.com, 2 pages.
Pearce et al. "Enteral feeding. Nasogastric, nasojejunal, percutaneous endoscopic gastrostomy, or jejunostomy: its indications and limitations," Postgrad Med. J., vol. 78, No. 918, pp. 198-204, (2002).
Anonymous "Public summary of opinion on orphan designation," www.ema.europa.eu 5 pages, (2012).
Levin "Wet Granulation: End-Point Determination and Scale-Up," pp. 1-40 (1999).
Agrawal et al. "Pharmaceutical Processing—A Review on Wet Granulation Technology," International Journal of Pharmaceutical Frontier Research, vol. 1 No. 1, pp. 65-83, (2011).
Barbiera et al. "Characteristics of the Action of Nitrimidazine (Nimorazole*) A New Systemic Trichomonacide," Boll. Chim. Farm., vol. 111 No. 9, pp. 541-554, (1972).
Toustrup "Development of a Hypoxia Targeted Gene Expression Classifier in Squamous Cell Carcinomas of the Head and Neck," PhD dissertation, pp. 1-58, (2011).
Anonymous "Nimorazole,"The Merck Index 14th edition, 1 page (2006).

DISPERSIBLE TABLET

The present invention relates to a pharmaceutical composition comprising Nimorazole, which tablet disintegrates in water. In particular, the invention concerns a pharmaceutical composition such as a tablet comprising Nimorazole or a pharmaceutically acceptable salt, for dispersion in water and administration via a tube to a patient with swallowing difficulties.

TECHNICAL BACKGROUND

The U.S. Pat. No. 4,371,540 describes the use of radiosensitizers for hypoxic cells. Administration is performed via an intravenous route or suggested to be done orally using a prodrug, wherein the prodrug is the acetate ester of the compound.

The U.S. Pat. No. 4,462,992 suggests administration parenterally, subcutaneously, intravenously, intramuscularly or intraperitoneally, or alternatively oral administration.

The patent application US 2010/322939 describes oral administration of Nimorazole 90 minutes prior to radiotherapy treatment.

According to Bowman, Corinne ("Administration of drugs to patients with swallowing difficulties", Journal of the Malta College of Pharmacy Practice, Issue 12 Winter 2007, pp. 42-45) patients who are unable to swallow due to a debilitating condition become dependent on an enteral feeding tube both for nutritional needs and for administration of medicines. Information regarding this mode of administration is very scarce and also associated with increased risk of tube obstruction, increased toxicity and reduced efficacy due to an inadequate administration method. Bowmann notes that "Unfortunately, crushing tablets is mistakenly taken for granted by some healthcare professionals without considering that the properties of the medication may be affected", and finally "Crushed tablets are the most frequent cause of obstruction of feeding tubes which results in increased morbidity and trauma to the patient besides the cost of replacing the tube. This may require surgical intervention".

SUMMARY OF THE INVENTION

Nimorazole is inter alia used to improve the efficacy of irradiation treatment for cancer patients.

Patients such as cancer patients may suffer from swallowing difficulties. In particular cancer patients undergoing irradiation treatment in the head and neck region and concurrent Nimorazole treatment may have difficulties swallowing Nimorazole tablets, and thus have a need for having Nimorazole administered via an alternative route. The amount of Nimorazole necessary for an effective treatment, such as about 2 g for each treatment, aggravates this problem, as it implies the use of large tablets or a high number of tablets.

Nimorazole is slightly soluble in water (The Merck Index, $14^{th}$ Edition). Experiments indicate that the solubility in water is about 5 mg/ml. Further, in order to achieve a reasonable dissolution rate, it is usually necessary to apply excessive amounts of liquid in order to obtain sink conditions. Preparing a bulky solution of Nimorazole for further distribution creates additional problems in terms of storage stability and difficulties distributing a large container comprising liquid.

There is a need for providing a liquid medium comprising an amount of Nimorazole exceeding the solubility limit of Nimorazole in water, in order to be able to administer effective amounts of Nimorazole via a feeding tube while avoiding the intake of excessive amounts of liquid medium. There is a need for being able to provide a liquid medium comprising Nimorazole within a short time frame. In addition, there is a need to provide a liquid medium comprising Nimorazole which is able to pass via a feeding tube without causing obstruction.

Attempts were made to provide a granulate comprising Nimorazole, which was formulated with the intent to be dispersed in water, administered via a feeding tube, and quickly dissolve in the stomach at low pH. However, the granulate suffered from the drawback that the granulate was not sufficiently dispersed in water at neutral pH, and thus created obstructions in a feeding tube. The development of the granulate comprising Nimorazole was subsequently stopped.

Attempts were made to provide a powder comprising Nimorazole, which was formulated to be quickly dispensed in water at neutral pH. Up to five sachets of powder had to be opened and carefully emptied into water, making sure that all the powder of each sachet was emptied completely. While this powder did not obstruct the feeding tube, it was seen as a quite tedious procedure that could impact patient compliance to the treatment. The development of the powder comprising Nimorazole was subsequently stopped. Further, the powder was less suitable for oral administration unless it was dispersed in water.

According to aspects and embodiments of the invention, the abovementioned problems are addressed by the present invention.

Surprisingly, it has been possible to provide a liquid medium comprising an amount of Nimorazole exceeding the solubility limit of Nimorazole in water, making it possible to administer effective amounts of Nimorazole via a feeding tube while avoiding the intake of excessive amounts of liquid medium. Further, it has been possible to provide a liquid medium comprising Nimorazole within a short time frame. In addition, it has been possible to provide a liquid medium comprising Nimorazole which is able to pass via a feeding tube without causing obstruction.

According to an aspect, the invention concerns a pharmaceutical composition comprising Nimorazole or a pharmaceutically acceptable salt thereof, for disintegration in water or an aqueous medium and administration via a tube.

A feeding tube may suitably be used. In particular, the invention concerns a pharmaceutical composition which allows administration using a feeding tube to a patient with swallowing difficulties.

The pharmaceutical formulation or tablet according to the invention preferably disintegrates upon contact with water, forming a dispersion. The forming of the dispersion may be aided by stirring in the water, or shaking a container comprising the tablet and water.

According to another aspect, the invention concerns a solid pharmaceutical composition comprising Nimorazole or a pharmaceutically acceptable salt thereof, and further comprising: a disintegrant; optionally one or more additional excipients; and a coating; said pharmaceutical composition allowing administration via at least two different routes:

i) oral administration, or
ii) disintegration in water or an aqueous medium to provide a dispersion, and subsequent administration of said dispersion via a tube.

Surprisingly, it has been possible to device a pharmaceutical formulation or tablet, which may be used directly for oral administration, and which alternatively may be dispersed in water in a short time frame for administration via a feeding tube. The pharmaceutical formulation or tablet may be dispersed in a small volume of water. The dispersed particles are sufficiently small to provide a slow sedimentation rate, allowing administration of the particles in dispersed state from e.g. a bottle via a feeding tube.

A pharmaceutical formulation in the form of a tablet is easy to handle and dosage may easily be measured and subsequently checked. Using a powder from individual sachets makes a dosing of several sachets cumbersome. Further, the use of a powder makes a dosage check after measurement of the intended dosage cumbersome, while a small number of tablets are easily counted for verification of dosage. Finally, a tablet provides a smaller surface area than a powder, thus potentially increasing the storage stability of the product.

According to an aspect, the invention concerns a kit of parts comprising a pharmaceutical composition according to the invention, and instructions for preparing a dispersion of said pharmaceutical composition for administration via a tube.

According to an aspect, the invention concerns a method for manufacturing a pharmaceutical formulation or tablet according to the invention, comprising wet granulation of Nimorazole.

Further information concerning wet granulation may be found in references such as: International Journal of Pharmaceutical Frontier Research, April-June 2011; 1(1):65-83, “Pharmaceutical Processing—A Review on Wet Granulation Technology”, Rajesh Agrawal and Yadav Naveen; “Wet Granulation: End-Point Determination and Scale-Up”, Michael Levin, Ph. D. Metropolitan Computing Corporation, East Hanover, N.J., USA; and Parikh D. “Handbook of Pharmaceutical Granulation Technology”, Marcel Dekker, Inc. New York, 1997.

According to an aspect, the invention concerns a method of treatment of cancer, wherein irradiation treatment is combined with the administration of at least one pharmaceutical formulation or tablet according to the invention, wherein said at least one pharmaceutical formulation or tablet is allowed to disintegrate in water or an aqueous medium and administered via a tube. This is particularly relevant when the patient has or acquires problems with swallowing, such as for cancer in the head and neck region.

This method is particularly preferred for patients with swallowing difficulties undergoing treatment with Nimorazole.

According to an aspect, the invention concerns a method of radiosensitizing hypoxic tumor cells comprising administering Nimorazole, wherein the administration comprises: providing a solid pharmaceutical composition comprising Nimorazole or a pharmaceutically acceptable salt thereof; dispersing said solid pharmaceutical composition in water or a an aqueous medium to obtain a dispersion; administering said dispersion via a tube.

According to an aspect, the invention concerns a use of a tablet according to the invention, wherein said tablet is dispersed in water and administered via a tube.

According to an aspect, the invention concerns an aqueous pharmaceutical composition comprising Nimorazole or a pharmaceutically acceptable salt thereof, wherein at least part of said Nimorazole or pharmaceutically acceptable salt thereof is dispersed in an aqueous medium in form of solid particles.

DETAILED DISCLOSURE

According to an embodiment, the invention concerns a pharmaceutical composition comprising Nimorazole or a pharmaceutically acceptable salt thereof, for disintegration in water or an aqueous medium and administration via a tube. A feeding tube may suitably be used.

The term “aqueous medium” covers the possibility of using water or water comprising one or more salts, such as a saline solution, and/or any (other) components for the patient, such as at least one active ingredient. It also covers the possibility of water comprising one or more nutrients, optionally with one or more active ingredients.

The pharmaceutical composition or tablet according to the invention preferably disintegrates upon contact with water, forming a dispersion. The forming of the dispersion may be aided by stirring in the water, or shaking a container comprising at least one tablet and water.

According to an embodiment, the invention concerns a pharmaceutical composition or a tablet for administration to a patient with swallowing difficulties.

According to an embodiment, the invention concerns a solid pharmaceutical composition comprising Nimorazole or a pharmaceutically acceptable salt thereof, and further comprising: a disintegrant; optionally one or more additional excipients, such as a binder; and a coating; said pharmaceutical composition allowing administration via at least two different routes: oral administration, or disintegration in water or an aqueous medium to provide a dispersion, and subsequent administration of said dispersion via a tube.

The solid pharmaceutical composition is preferably a tablet.

The pharmaceutical composition is preferably provided in a solid form which is stable over time.

The disintegrant makes it possible to provide a dispersion in a short time interval. Preferably, the solid pharmaceutical composition allows the provision of a dispersion comprising an amount of Nimorazole or a pharmaceutically acceptable salt thereof, wherein the amount of Nimorazole or a pharmaceutically salt thereof exceeds the solubility limit of Nimorazole in the water or the aqueous medium. Preferably, the solid pharmaceutical composition allows the provision of a dispersion comprising an amount of Nimorazole or a pharmaceutically acceptable salt thereof, wherein the amount of Nimorazole or a pharmaceutically salt thereof exceeds the 5 mg/ml of water or the aqueous medium.

The coating may serve as taste-masking, as Nimorazole has an unpleasant taste. An unpleasant taste may lower patient compliance. Additionally, a coating may improve storage stability of the pharmaceutical formulation.

Having a pharmaceutical composition which allows two different routes of administration carries a number of advantages. Firstly, patient compliance is improved, as the patient is already used to the pharmaceutical composition if or when the patient needs to change route of administration. Secondly, the costs associated with production and receiving marketing approval are lowered, as only one product needs to be produced and approved.

Preferably the dispersion of the solid pharmaceutical composition may be done by the patient. It is further preferred that administration of the dispersion may be performed by the patient. This allows out-patient or ambulatory use.

An excipient is generally a pharmacologically inactive substance. Examples include, but are not limited to, diluents, disintegrants, binders, glidants, lubricants, and coatings. Other examples of suitable excipients may be found in Handbook of Pharmaceutical Excipients, Pharmaceutical Press, London.

Diluents are inactive ingredients that are added to tablets and capsules in addition to the active drug. Some very common diluents in tablets include starch, cellulose derivatives, and magnesium stearate (also a lubricant). Diluents fill out the size of a tablet or capsule, making it practical to produce and convenient for the consumer to use. By increasing the bulk volume, diluents make it possible for the final product to have the proper volume for patient handling. A good diluent must be inert, compatible with the other components of the formulation, non-hygroscopic, relatively cheap, compactible, and preferably tasteless or pleasant tasting. Plant cellulose (pure plant Diluent) is a popular diluent in tablets or hard gelatin capsules. Dibasic calcium phosphate is another popular tablet diluent. A range of vegetable fats and oils can be used in soft gelatin capsules. Other examples of diluents include: lactose, sucrose, glucose, mannitol, sorbitol, calcium carbonate, and magnesium stearate.

Disintegrants expand and dissolve when wet causing the tablet to break apart. They ensure that when the tablet is in contact with water, it rapidly breaks down into smaller fragments, facilitating dissolution or dispersion. Examples of disintegrants include, but are not limited to: Crosslinked polymers, such as crosslinked polyvinylpyrrolidone (crospovidone), and crosslinked sodium carboxymethyl cellulose (croscarmellose sodium); and the modified starch sodium starch glycolate. Specific examples further include Indian 414, L-HPC, and pregelatinised starch.

Binders hold the ingredients in a tablet together. Binders ensure that tablets and granules can be formed with required mechanical strength, and give volume to tablets. Examples of binders include: Saccharides and their derivatives: Disaccharides, sucrose, lactose; Polysaccharides and their derivatives, such as starches, cellulose or modified cellulose, such as microcrystalline cellulose and cellulose ethers such as hydroxypropyl cellulose (HPC); Sugar alcohols such as xylitol, sorbitol or maltitol; Further Protein: gelatin; and Synthetic polymers: polyvinylpyrrolidone (PVP), polyethylene glycol (PEG). Examples include gelatin, cellulose, cellulose derivatives, polyvinylpyrrolidone, starch, sucrose and polyethylene glycol. Other examples include cellulose, methyl cellulose, polyvinylpyrrolidone and polyethylene glycol.

Glidants are used to promote powder flow by reducing interparticle friction and cohesion. These are used in combination with lubricants as they have no ability to reduce die wall friction. Examples include fumed silica, talc, and magnesium carbonate.

Lubricants are agents added to tablet and capsule formulations to improve certain processing characteristics. Lubricants inter alia prevent ingredients from clumping together and from sticking to the tablet punches or capsule filling machine. Lubricants also ensure that tablet formation and ejection can occur with low friction between the solid and die wall. Common minerals like talc or silica, and fats, e.g. vegetable stearin, magnesium stearate or stearic acid are examples of lubricants used in tablets or hard gelatin capsules.

Coatings protect ingredients from deterioration by moisture in the air and make large or unpleasant-tasting tablets easier to swallow. For most coated tablets, a cellulose ether hydroxypropyl methylcellulose (HPMC) film coating is used which is free of sugar and potential allergens. Occasionally, other coating materials are used, for example synthetic polymers, shellac, corn protein zein or other polysaccharides. A specific example is Opadry. Capsules are coated with gelatin.

According to an embodiment, the invention concerns a solid pharmaceutical composition comprising Nimorazole or a pharmaceutically acceptable salt thereof, and further comprising: diluent; disintegrant; binder; glidant; lubricant; and optionally one or more additional excipients; and a coating.

According to an embodiment, the invention concerns a solid pharmaceutical composition comprising Nimorazole or a pharmaceutically acceptable salt thereof, and further comprising: Diluent, 1-50%; Disintegrant, 0.5-15%; Binder, 0.5-15%; Glidant, 0.5-3%; Lubricant, 0.5-3%; and optionally one or more additional excipients; and a Coating, 0.5-5%.

According to an embodiment, the invention concerns a solid pharmaceutical composition comprising Nimorazole or a pharmaceutically acceptable salt thereof, and further comprising: Diluent, 2-25%, preferably 4-15%, more preferred 6-10%, preferably 7-9%; Disintegrant, 1-12%, preferably 3-10%, more preferred 5-9%, preferably 7-8%; Binder, 1-10%, preferably 2-8%, more preferred 3-6%, preferably 4-5%; Glidant, 0.6-2.5%, preferably 0.8-2%, more preferred 0.9-1.8%, preferably 1-1.5%; Lubricant, 0.6-2.5%, preferably 0.8-2%, more preferred 0.9-1.8%, preferably 1-1.5%; and optionally one or more additional excipients; and a Coating, 0.7-4%, preferably 1-3%, more preferred 1.5-2.5%, preferably 2-2.2%.

According to an embodiment, the invention concerns a solid pharmaceutical composition comprising Nimorazole or a pharmaceutically acceptable salt thereof, and further comprising:

a) An Intragranular part, comprising: Diluent; Disintegrant; and Binder; and
b) An Extragranular part, comprising: Diluent; Disintegrant; Glidant; and Lubricant; and
c) A Coating.

According to an embodiment, the invention concerns a solid pharmaceutical composition comprising Nimorazole or a pharmaceutically acceptable salt thereof, and further comprising:

a) An Intragranular part, comprising: Diluent, 1-50%; Disintegrant, 0.5-15%; and Binder, 0.5-15%; and
b) An Extragranular part, comprising: Diluent, 0.5-50%; Disintegrant, 0.5-15%; Glidant, 0.5-3%; and Lubricant, 0.5-3%; and
c) A Coating, 0.5-5%.

According to an embodiment, the invention concerns a solid pharmaceutical composition comprising Nimorazole or a pharmaceutically acceptable salt thereof, and further comprising:

a) An Intragranular part, comprising: Diluent, 2-25%, preferably 4-15%, more preferred 6-10%, preferably 7-8%; Disintegrant, 0.7-10%, preferably 1-8%, more preferred 1.5-5%, preferably 2-3%; and Binder, 1-10%, preferably 2-8%, more preferred 3-6%, preferably 4-5%; and
b) An Extragranular part, comprising: Diluent, 0.7-25%, preferably 0.8-10%, more preferred 0.9-5%, preferably 1-2%; Disintegrant, 1-10%, preferably 2-8%, more preferred 4-7%, preferably 5-6%; Glidant, 0.6-2.5%, preferably 0.8-2%, more preferred 0.9-1.8%, preferably 1-1.5%; and Lubricant, 0.6-2.5%, preferably 0.8-2%, more preferred 0.9-1.8%, preferably 1-1.5%; and
c) A Coating, 0.7-4%, preferably 1-3%, more preferred 1.5-2.5%, preferably 2-2.2%.

According to an embodiment, the invention concerns a pharmaceutical composition which is an immediate release tablet. An immediate release tablet disintegrates in water within 30 minutes.

According to an embodiment, the invention concerns a pharmaceutical composition or a tablet for disintegration in water within 15 minutes, preferably 10 minutes, more preferred 5 minutes, preferably within 3 minutes to produce a dispersion for administration to a patient via a tube.

According to an embodiment, the invention concerns a pharmaceutical composition or a tablet, wherein said dispersion passes through a sieve screen with a nominal mesh aperture of 710 μm.

According to an embodiment, the invention concerns a pharmaceutical composition or a tablet, which disintegrates within 10 min., preferably within 5 min., using water at 25° C., preferably 20° C., more preferred at 15° C.

According to an embodiment, the invention concerns a pharmaceutical composition which is a dispersible tablet. Dispersible tablets are intended to be dispersed in water before administration, providing a homogeneous dispersion. Dispersible tablets disintegrate within 3 minutes using water at 15-25° C. The fineness of dispersion should comply with a test comprising placing 2 tablets in 100 ml water and stirring until completely dispersed. A smooth dispersion is produced, which passes through a sieve screen with a nominal mesh aperture of 710 μm.

According to an embodiment, the invention concerns a pharmaceutical composition or a tablet, which allows complete dispersion of one or more pharmaceutical compositions or tablets comprising a total of at least 1000 mg Nimorazole in 100 ml water at 25° C. upon stirring, thereby providing a dispersion; said dispersion passing through a sieve screen with a nominal mesh aperture of 710 μm. According to embodiments, the term "complete dispersion" covers the case wherein at least 90%, more preferred at least 95%, preferably at least 98%, more preferred 99%, preferably 100% Nimorazole is dispersed or dissolved.

According to an embodiment, the invention concerns a pharmaceutical composition or a tablet for administration via a feeding tube.

According to an embodiment, the invention concerns a pharmaceutical composition or a tablet for administration via a feeding tube selected among the group consisting of a percutaneous endoscopic gastrostomy tube, a nasogastric feeding tube, a nasojejunal feeding tube, a gastric feeding tube, and a jejunostomy feeding tube.

According to an embodiment, the invention concerns a pharmaceutical composition or a tablet for administration via a percutaneous endoscopic gastrostomy ("PEG") tube or a nasogastric ("NG") feeding tube.

According to an embodiment, the invention concerns a pharmaceutical composition or a tablet for treatment of bedridden or geriatric patients. These patient groups often suffer from difficulties swallowing tablets.

According to an embodiment, the invention concerns a pharmaceutical composition or a tablet for treatment of patients undergoing irradiation treatment, particularly irradiation treatment of the head and/or neck region.

According to an embodiment, the invention concerns a pharmaceutical composition or a tablet for treatment of intubated patients, such as patients having inserted a tube into the gastrointestinal tract. Individual differences may influence if and at what point during a treatment regime patients are intubated.

According to an embodiment, the invention concerns a pharmaceutical composition or a tablet for treatment of patients having received at least a number selected among 1, 2, 3, 4, 5, 6, 7, 8, 9 or 10 irradiation treatments for cancer of the head and/or neck region.

While Nimorazole is usually administered from the first irradiation treatment, using a tube becomes particularly relevant when the patient begins to experience problems swallowing, usually from the 5th or 6th irradiation treatment.

Thus, the need for administration of Nimorazole via a feeding tube does usually not occur before after the $4^{th}$ or $5^{th}$ irradiation treatment, as the swallowing difficulties is usually not present early. During the first about four fractions of irradiation treatment direct oral administration is preferred, i.e. in the form of a tablet taken orally, while the need for administration via a feeding tube usually occurs later, i.e. from the $5^{th}$ or $6^{th}$ irradiation treatment.

Hence, for a Nimorazole tablet to be used with concurrent radiotherapy, it is convenient to have a tablet which may both be administered directly orally, and which may be used for making a dispersion or solution for administration via a feeding tube. However, due to the unpleasant taste of Nimorazole, it is preferable that the tablet comprises a coating, masking the taste. Conventional coatings suffers from the drawback that they make it difficult to make a dispersion, and parts of the coating may get stuck in a feeding tube.

According to an embodiment, the invention concerns a pharmaceutical composition or a tablet for swallowing or for disintegration in water or an aqueous medium and administration via a tube.

This tablet is specifically adapted to allow swallowing or allow disintegration in water or an aqueous medium at the discretion of a person administering the tablet.

According to an embodiment, the invention concerns a pharmaceutical composition or a tablet further comprising a coating facilitating swallowing and masking the taste of Nimorazole.

The taste of Nimorazole is unpleasant to most patients. Thus, without a coating, many patients will feel the swallowing of Nimorazole tablets objectionable. However, a coating tends to impede the disintegration of the tablet in water. Surprisingly, it has been possible to device a coating, which facilitates swallowing, and masks the taste of Nimorazole, and still allows producing a dispersion in water quickly.

According to an embodiment, the invention concerns a pharmaceutical composition or a tablet for curative or palliative treatment of cancer in patients undergoing radiotherapy, particularly for patients with cancer in the head and/or neck region.

According to an embodiment, the invention concerns a pharmaceutical composition or a tablet for treatment of patients with hypoxic cancer. Methods for testing whether cancers are hypoxic are known in the art.

According to an embodiment, the invention concerns a pharmaceutical composition or a tablet for treatment of an indication selected among breast cancer, head/neck cancer, lymphoma, cervical cancer, colorectal cancer, brain cancer, lung cancer, bladder cancer, and prostate cancer. The invention is particularly relevant for patients with a swallowing problem, which may or may not be caused by irradiation treatment. The cancer treatment may be with or without concurrent chemotherapy.

According to an embodiment, the invention concerns a pharmaceutical composition or a tablet for treatment of head/neck cancer.

According to an embodiment, the invention concerns a pharmaceutical composition or a tablet for treatment of cervical cancer or inoperable lung cancer.

According to an embodiment, the invention concerns a pharmaceutical composition or a tablet for treatment of non-smokers. Nimorazole may appear to have reduced or little influence on the efficacy of irradiation treatment of cancer among patients who have not stopped smoking during treatment. According to an embodiment, cessation of smoking during therapy is warranted.

According to an embodiment, the invention concerns a pharmaceutical composition, comprising at least 250 mg Nimorazole or a pharmaceutically acceptable salt thereof.

According to an embodiment, the invention concerns a pharmaceutical composition, comprising 10-2500 mg, more preferred 100-2000 mg, preferably 300-1500 mg, more preferred 400-1000 mg, preferably 500 mg Nimorazole or a pharmaceutically acceptable salt thereof.

According to an embodiment, the invention concerns a pharmaceutical composition or a tablet, subject to the proviso that 3-5 of said pharmaceutical compositions or tablets may be dispersed in 2 dl water at 25° C., preferably 20° C., more preferred 15° C. within 15, preferably 10, more preferred 5, preferably within 3 minutes.

According to an embodiment, the invention concerns a pharmaceutical composition or a tablet allowing dispersion of 1500-2500 mg, preferably 2000 mg, Nimorazole in 2 dl water at 25° C., preferably 20° C., more preferred 15° C. within 15, preferably 10, more preferred 5, preferably within 3 minutes.

According to an embodiment, the invention concerns a pharmaceutical composition or a tablet for treatment alone or combined with chemotherapy. According to an embodiment, the concerns a tablet for treatment alone or combined with chemotherapy in patients undergoing irradiation of a total of ≥40 Grey during a course of treatment.

According to an embodiment, the invention concerns a kit of parts comprising a pharmaceutical composition according to the invention, and instructions for preparing a dispersion of said pharmaceutical composition for administration via a tube.

According to an embodiment, the invention concerns a method for manufacturing a pharmaceutical composition, comprising wet granulation of Nimorazole.

According to an embodiment, the invention concerns a method of treatment of cancer, wherein irradiation treatment is combined with the administration of at least one tablet according to the invention, wherein said at least one tablet is allowed to disintegrate in water or an aqueous medium and administered via a tube. This method is particularly preferred for patients with swallowing difficulties undergoing treatment with Nimorazole.

According to an embodiment, the invention concerns a method of radiosensitizing hypoxic tumor cells comprising administering Nimorazole, wherein the administration comprises: Providing a solid pharmaceutical composition comprising Nimorazole or a pharmaceutically acceptable salt thereof; Dispersing said solid pharmaceutical composition in water or a an aqueous medium to obtain a dispersion; and Administering said dispersion via a tube.

Patients receiving Nimorazole in form of tablets may have difficulties swallowing. A new route or way of administration of Nimorazole particularly suitable for these patients is suggested. There is a need for a pharmaceutical composition, which may be administered via a tube without the need of crushing tablets. The dispersion to be administered may easily be prepared by the patient, in particular without the need to crush tablets. Thus, this is particularly suitable for out-patient administration, i.e. patients receiving Nimorazole as part of ambulatory treatment, e.g. patients who are requested to take the treatment in the home or on the way to the hospital before irradiation treatment at a treatment facility such as a hospital. Further, there is a need of taste-masking pharmaceutical compositions or tablets comprising Nimorazole.

According to an embodiment, the invention concerns a use of a tablet according to the invention, wherein said tablet is dispersed in water and administered via a tube.

According to an embodiment, the invention concerns an aqueous pharmaceutical composition comprising Nimorazole or a pharmaceutically acceptable salt thereof, wherein at least part of said Nimorazole or pharmaceutically acceptable salt thereof is dispersed in an aqueous medium in form of solid particles.

According to an embodiment, the invention concerns an aqueous pharmaceutical composition obtainable by dispersing a pharmaceutical composition in water or an aqueous medium.

According to an embodiment, the invention concerns an aqueous pharmaceutical composition, wherein said Nimorazole or pharmaceutically acceptable salt is present in a concentration exceeding 5 mg/ml aqueous medium.

According to an embodiment, the invention concerns a solid pharmaceutical composition comprising:

i) nimorazole or a pharmaceutically acceptable salt thereof;

ii) a disintegrant;

iii) optionally one or more additional excipients; and iv) a coating;

said pharmaceutical composition allowing administration to a patient via both oral administration and a feeding tube, wherein prior to administration via a feeding tube the pharmaceutical composition is disintegrated in an aqueous medium to provide a dispersion which is administered via the feeding tube.

According to an embodiment, the invention concerns the pharmaceutical composition wherein the additional excipients comprise a diluent, a binder, a glidant, and a lubricant.

According to an embodiment, the invention concerns the pharmaceutical composition comprising:

diluent, 1-50 wt %;
disintegrant, 0.5-15 wt %;
binder, 0.5-15 wt %;
glidant, 0.5-3 wt %;
lubricant, 0.5-3 wt %;
optionally one or more additional excipients; and
a coating, 0.5-5 wt %.

According to an embodiment, the invention concerns the pharmaceutical composition comprising:

diluent, 7-9 wt %;
disintegrant, 7-8 wt %;
binder, 4-5 wt %;
glidant, 1-1.5 wt %;
lubricant, 1-1.5 wt %;
optionally one or more additional excipients; and
a coating, 2-2.2 wt %.

According to an embodiment, the invention concerns the pharmaceutical composition comprising:

an intragranular part, comprising a diluent, a disintegrant, and a binder;

an extragranular part, comprising a diluent, a disintegrant, a glidant, and a lubricant; and a coating.

According to an embodiment, the invention concerns the pharmaceutical composition that is formulated as a tablet, an immediate release tablet or a dispersible tablet.

According to an embodiment, the invention concerns the pharmaceutical composition that disintegrates in water at 20° C. within 5 minutes.

According to an embodiment, the invention concerns the pharmaceutical composition that after disintegration in an aqueous medium passes through a sieve screen with a nominal mesh aperture of 710 μm.

According to an embodiment, the invention concerns the pharmaceutical that can be dispersed to provide at least 1000 mg nimorazole in 100 ml water at 25° C. within 5 minutes upon stirring, wherein said dispersion passes through a sieve screen with a nominal mesh aperture of 710 μm.

According to an embodiment, the invention concerns the pharmaceutical composition, wherein the feeding tube is selected from the group consisting of a percutaneous endoscopic gastrostomy tube, a nasogastric feeding tube, a nasojejunal feeding tube, a gastric feeding tube, and a jejunostomy feeding tube.

According to an embodiment, the invention concerns the pharmaceutical composition, wherein the coating facilitates swallowing and masks the taste of nimorazole.

According to an embodiment, the invention concerns the pharmaceutical composition, wherein the composition comprises at least 250 mg nimorazole or a pharmaceutically acceptable salt thereof per dosing unit.

According to an embodiment, the invention concerns the pharmaceutical composition that can be dispersed to provide at least 2000 mg of nimorazole or a pharmaceutically acceptable salt thereof in 2 dl of water at 25° C. within 3 minutes.

According to an embodiment, the invention concerns a kit of parts comprising the pharmaceutical composition and instructions for preparing a dispersion of the pharmaceutical composition for administration to a patient via a feeding tube.

According to an embodiment, the invention concerns a kit of parts comprising:

a) a solid pharmaceutical composition comprising:

i) nimorazole or a pharmaceutically acceptable salt thereof;

ii) a disintegrant;

iii) optionally one or more additional excipients; and iv) a coating;

said pharmaceutical composition allowing administration to a patient via a feeding tube by disintegrating the solid pharmaceutical composition in an aqueous medium to provide a dispersion which is administered via the feeding tube; and b) instructions for disintegrating the solid pharmaceutical composition in an aqueous medium to form a dispersion and administering the dispersion via a feeding tube.

According to an embodiment, the invention concerns the pharmaceutical composition, made by a method comprising performing wet granulation of a composition comprising nimorazole or a pharmaceutically acceptable salt thereof.

According to an embodiment, the invention concerns a method for manufacturing a pharmaceutical composition, the method comprising performing wet granulation of nimorazole.

According to an embodiment, the invention concerns a method of treating cancer by radiosensitizing hypoxic tumor cells, the method comprising performing radiation treatment combined with the administration of at least one solid pharmaceutical composition comprising:

i) nimorazole or a pharmaceutically acceptable salt thereof;

ii) a disintegrant;

iii) optionally one or more additional excipients; and iv) a coating;

wherein said at least one solid pharmaceutical composition is allowed to disintegrate or is dispersed in an aqueous medium and administered to a patient via a feeding tube.

According to an embodiment, the invention concerns a method of treating cancer by radiosensitizing hypoxic tumor cells, the method comprising performing radiation treatment combined with the administration of at least one solid pharmaceutical composition, wherein said at least one solid pharmaceutical composition is allowed to disintegrate or is dispersed in water or an aqueous medium and administered to a patient via a tube.

According to an embodiment, the invention concerns the method, wherein the radiation treatment comprises:

providing said solid pharmaceutical composition comprising nimorazole or a pharmaceutically acceptable salt thereof;

dispersing the solid pharmaceutical composition in water or a an aqueous medium to obtain a dispersion;

administering the dispersion to a patient via a feeding tube; and administering radiation to the patient.

According to an embodiment, the invention concerns the method, wherein the dispersion contains said nimorazole or pharmaceutically acceptable salt thereof at a concentration exceeding 5 mg/ml of the aqueous medium.

According to an embodiment, the invention concerns the method, further comprising administering chemotherapy to the patient.

According to an embodiment, the invention concerns the method, wherein the cancer is selected from the group consisting of breast cancer, head/neck cancer, lymphoma, cervical cancer, colorectal cancer, brain cancer, lung cancer, bladder cancer, and prostate cancer.

According to an embodiment, the invention concerns a dispersion containing dispersed particulate nimorazole or a pharmaceutically acceptable salt thereof in an aqueous medium, wherein the concentration of nimorazole or its pharmaceutically acceptable salt exceeds the solubility limit thereof in the aqueous medium, and wherein the dispersion is formulated for administration to a patient via a feeding tube.

According to an embodiment, the invention concerns the aqueous dispersion, wherein the particulate nimorazole or its pharmaceutically acceptable salt has an average diameter of less than 710 μm.

All cited references are incorporated by reference.

The following Examples are provided to explain rather than limit the present invention. It will be clear to the person skilled in the art that aspects, embodiments and claims of the present invention may be combined.

Unless otherwise mentioned, all percentages are in w/w.

EXAMPLES

Examples A1, A2, A3, and A4

Tablet ingredients and manufacture

| Name of ingredient | Specification | Tablet A1 mg/tablet | Tablet A2 mg/tablet | Tablet A3 mg/tablet | Tablet A4 mg/tablet |
|---|---|---|---|---|---|
| Intragranular | | | | | |
| Nimorazole | INH. | 500 | 500 | 500 | 500 |
| Cellulose microcrystalline (Avicel PH 101) | Ph. Eur. | 50 | 50 | 50 | 34 |
| Sodium Starch Glycolate | | 14 | | | |
| Crospovidone (Kollidon CL) | Ph. Eur. | | 14 | 14 | 19.5 |
| Povidone K30 [Binder] | Ph. Eur. | 28 | 28 | 28 | 28 |
| Purified water | BP | Q.S. | Q.S. | Q.S. | Q.S. |
| Extragranular | | | | | |
| Cellulose microcrystalline (Avicel 102) | Ph. Eur. | 9 | 9 | 9 | 9 |
| Crospovidone (Kollidon CL) | Ph. Eur. | 35 | 35 | 35 | 45.5 |
| Silica Colloidal anhydrous (Cab-o-sil) | Ph. Eur. | 7 | 7 | 7 | 7 |

-continued

Tablet ingredients and manufacture

| Name of ingredient | Specification | Tablet A1 mg/ tablet | Tablet A2 mg/ tablet | Tablet A3 mg/ tablet | Tablet A4 mg/ tablet |
|---|---|---|---|---|---|
| Magnesium Stearate (VG) | Ph. Eur. | 7 | 7 | 7 | 7 |
| Total weight of core tablet | | 650 | 650 | 650 | 650 |
| Film Coating | | | | | |
| Opadry 03B57695 Grey | INH. | 6.5 | 6.5 | 13 | 16.25 |
| Purified water | BP | 58.5 | 58.5 | 117 | Q.S. |
| Total weight of coated tablet | | 656.5 | 656.5 | 663 | 666.25 |

Purified water evaporates during process and does not appear in finished product.

Unless otherwise mentioned, the environmental conditions are about 22° C. Crospovidone was replaced with Sodium Starch Glycolate for Tablet A1. Tablets were manufactured using the following steps.

i. Sifting with vibratory sifter: Crospovidone was mixed with cellulose microcrystalline PH 101 and finally mixed with Nimorazole. The material was sifted through a 30# sieve using vibratory sifter.

ii. Binder preparation and binder addition: Povidone K30 was dispersed into weighed quantity of purified water to prepare a 20% w/w dispersion under stirring.

iii. Dry mixing in rapid mixer granulator: The sifted material from step i. was loaded into Rapid Mixer Granulator, and the material dry mixed for 10 min at slow speed of impeller, keeping Chopper off.

iv. Wet mixing: The binder of step ii. was added into step iii. within 2 minutes with slow speed of impeller, keeping Chopper off. If required, additional sufficient quantity of purified water was added within one min.

v. The wet mass of step iv. was mixed up to 1 minute with slow speed of impeller and slow speed chopper to get uniform consistency of the wet mass. The wet mass was discharged from Rapid Mixer Granulator with impeller at slow speed.

vi. Wet milling in co-mill: The wet mass of step v. was passed through a 8.00 mm screen using co-mill at 700 RPM.

vii. Drying in fluidized bed processor/dryer of the wet granular mass was performed with an inlet temperature of 60±10° C., ensuring uniform drying, until loss on drying (% LOD) was obtained. The percent loss on drying (% LOD) of the granules was determined at 105° C. in auto mode in moisture analyzer, and drying was continued until % LOD reached within the limit, in the range of 1.5 to 3.0%.

viii. Sizing: The dried granules obtained in step vii. were sifted through a 20# sieve using Vibratory sifter to get uniform sized granules.

ix. 20# retained granules of step viii. were sifted through 14#. 14# retained and 14# passed granules were collected separately.

x. The 14# retained granules obtained in step ix. were milled through 2.0 mm SS screen using co-mill at 700 RPM. The milled granules were passed through 20# sieve using vibro sifter.

xi. Both the oversized granules obtained in step x. and 14# passed 20# retained fraction of step ix. were milled through 1.0 mm SS screen using co-mill at 700 RPM. The milled granules were passed through 20# sieve using vibro sifter.

xii. All the granules were finally sifted through 20# SS sieve using vibratory sifter.

xiii. Blending & Lubrication in pillar type bin blender: Extragranular cellulose microcrystalline and crospovidone was sifted through 40# sieve using vibratory sifter. Subsequently, this was blended with the sifted granules for 10 minutes. Separately, silica colloidal anhydrous and magnesium stearate was sifted through 30# sieve using vibratory sifter. The mixture was added, and lubrication performed for 3 minutes.

xiv. Compression in rotary press tablet compression machine. Tablets with average weight of 650 mg were produced, having a disintegration time of not more than 15 minutes.

xv. Coating dispersion preparation in stirrer: Opadry 03B57695 Grey was dispersed in to weighed quantity of purified water to prepare a 10% w/w dispersion under stirring.

xvi. Coating in autocoater: The compressed core tablets were sprayed with the film coating dispersion. The curing was at 45° C. inlet temperature.

xvii. Packaging in blister packing machine.

Tablets A1, A2, A3 and A4 are all suitable for oral administration as well as dispersion in water before being administered via a feeding tube. The tablets differed in terms of time necessary for dispersion and storage stability. Preliminary experiments indicate the amount of coating provides a trade-off between storage stability and dispersion time.

More coating tend to provide improved storage time but also increased time for disintegration or dispersion.

Example B

Nimorazole Coated Tablets Comprising Crospovidone—General Recipe

Dry mix containing Nimorazole, cellulose microcrystalline, crospovidone, granulated using granulating fluid, dried and sized. Granules further blended and lubricated with extragranular material and compressed in to tablets. Core tablets further film coated. Tablets deliver 500 mg of Nimorazole.

| Sr. No. | Name of Ingredient | Category | Qty. Per Tablet [range] | Qty. Per Tablet (mg) [Actual] |
|---|---|---|---|---|
| Intragranular | | | | |
| 01. | Nimorazole | Active ingredient | 500.000 mg | 500.000 |
| 02. | Cellulose microcrystalline (Avicel PH 101) | Diluent | 1-50% | 50.000 (7.69%) |
| 03. | Crospovidone (Kollidon CL) | Disintegrant | 0.5-15% | 14.000 (2.154%) |
| 04 | Povidone K30 | Binder | 0.5-15% | 28.00 (4.30%) |
| 05 | Purified Water | | Q.S. | Q.S. |
| Extragranular | | | | |
| 06. | Cellulose microcrystalline (Avicel 102) | Diluent | 0.5-50% | 9.000 (1.385%) |
| 07. | Crospovidone (Kollidon CL) | Disintegrant | 0.5-15% | 35.000 (5.385%) |
| 08 | Silica Colloidal anhydrous (Cab-o-Sil) | Glidant | 0.5-3% | 7.000 (1.07%) |

-continued

| Sr. No. | Name of Ingredient | Category | Qty. Per Tablet [range] | Qty. Per Tablet (mg) [Actual] |
|---|---|---|---|---|
| 09 | Magnesium Stearate (VG) | Lubricant | 0.5-3% | 7.000 (1.07%) |
| | | Coating | | |
| 10. | Opadry 03B57695 Grey | Coating | 0.5-5% | 13.00 (2.0%) |

Example C

Nimorazole Tablets Comprising Sodium Starch Glycolate—General Recipe

Dry mix containing Nimorazole, cellulose microcrystalline, Sodium starch glycolate, granulated using granulating fluid, dried and sized. Granules further blended and lubricated with extragranular material and compressed in to tablets. Tablets deliver 500 mg of Nimorazole.

These tablets have no coating. The absence of a coating means that some patients dislike swallowing the tablets due to the unpleasant taste of the active ingredient.

| Sr. No. | Name of Ingredient | Qty. Per Tablet [range] | Qty. Per Tablet (mg) [Actual] |
|---|---|---|---|
| | Intragranular | | |
| 01. | Nimorazole | 500.000 mg | 500.000 |
| 02. | Cellulose microcrystalline (Avicel PH 101) | 1-50% | 50.000 (7.69%) |
| 03. | Sodium starch glycolate | 0.5-15% | 14.000 (2.154%) |
| 04 | Povidone K30 | 0.5-15% | 28.00 (4.30%) |
| 05 | Purified Water | Q.S. | Q.S. |
| | Extragranular | | |
| 06. | Cellulose microcrystalline (Avicel 102) | 0.5-50% | 9.000 (1.385%) |
| 07. | Sodium starch glycolate | 0.5-15% | 35.000 (5.385%) |
| 08 | Silica Colloidal anhydrous (Cab-o-Sil) | 0.5-3% | 7.000 (1.07%) |
| 09 | Magnesium Stearate (VG) | 0.5-3% | 7.000 (1.07%) |

Example D

Nimorazole Oral Powder

Dry mix of Nimorazole, Citric acid Anhydrous, Aspartame, Mannitol and Sucrose granulated using granulating fluid to prepare granules. Granules dried and sized and blended with flavor. Blend packed in single unit dosage form i.e. sachet. When one sachet is dispersed in 250 ml water yields a dispersion which delivers 500 mg of Nimorazole.

This oral powder is less suited for direct oral administration without being dispersed in water.

| Sr. No. | Name of Ingredient | Qty. Per Sachet (range) | Qty. Per Sachet(mg) (Actual) |
|---|---|---|---|
| | Intragranular | | |
| 01. | Nimorazole | 500.00 mg | 500.00 |
| 02. | Citric acid Anhydrous | 0.5-15% | 40.00 (3.13%) |

-continued

| Sr. No. | Name of Ingredient | Qty. Per Sachet (range) | Qty. Per Sachet(mg) (Actual) |
|---|---|---|---|
| 03. | Aspartame | 0.5-25% | 250.00 (19.6 %) |
| 04 | Mannitol | 0.5-50% | 185.00 (14.51%) |
| 05 | Sucrose | 0.5-50% | 100.00 (7.84%) |
| 06. | Purified Water | Q.S. | Q.S. |
| | Extragranular | | |
| 07. | Flavor | 0.5-50% | 40 (3.17%) |
| 08 | NAT FL Modulator (Sweet) FMT TM P | 0.5-50% | 160 (12.5%) |

Example E

Nimorazole Oral Granules

Nimorazole, Cellulose Microcrystalline, Silica Colloidal Anhydrous, Maize Starch, Hydroxypropylcellulose, Povidone granulated by spraying granulating fluid by using Top spray assembly. Granules further coated with basic butylated methacrylate copolymer hydro-alcoholic solution. Quantity equivalent to unit dose packed in sachet dispersed in 250 ml of water delivers 500 mg.

These granules have a tendency to clog a feeding tube, when the granules are allowed to disintegrate or disperse in water.

| Sr. No. | Name of Ingredient | Qty. Per Dose (range) | Qty. Per Dose (mg) (Actual) |
|---|---|---|---|
| | Core granules | | |
| 01. | Nimorazole | 500 mg | 500 mg |
| 02. | Cellulose Microcrystalline (Avicel 101) | 0.5-50% | 140* (19.8%) |
| 03. | Silica Colloidal Anhydrous | 0.5-3% | 5.00* (0.7%) |
| 04 | Maize Starch | 0.5-15% | 22.00* (3.11) |
| 05 | Hydroxypropylcellulose (HPC-L) | 0.5-15% | 7.50* (1.06%) |
| 06. | Povidone (Dry Mixing) | 0.5-15% | 5.00* (0.7%) |
| 07. | Povidone (Binding) | 0.5-15% | 20.00* (2.82%) |
| 08. | Purified Water | q.s. | q.s. |
| | Extragranular | | |
| 09. | Talc | 0.25-3% | 5.25 (0.74%) |
| 10. | Silica Colloidal Anhydrous | 0.15-3% | 1.75 (0.25%) |
| | Coated Granules<br>Coating Dispersion Ingredient | | |
| 11. | Basic Butylated Methacrylate Copolymer | 0.5-10% | 26.25* (3.71%) |
| 12. | Macrogol 6000 | 2-30% | 2.625@ (10.0%) |
| 13. | Talc | 5-50% | 13.125@ (50%) |
| 14. | Silica Colloidal Anhydrous | 0.5-3% | 0.058@ (0.22%) |
| 15. | Isopropyl Alcohol | q.s | q.s |
| 16. | Purified Water<br>Total weight | q.s | q.s |
| | Lubrication of coated Granules | | |
| 17. | Talc | 0.05-3% | 0.800 |
| 18. | Silica Colloidal Anhydrous | 0.02-3% | 0.354 |

* Quantity expressed as % w/w of core granules
@ Quantity expressed as % w/w of Polymer weight Disintegration and Solubility Experiments indicate the solubility of Nimorazole in water is 4.91 mg/ml.

Tablet A1

Tablets A1 had a thickness of 5.61 to 5.65 mm. The disintegration time was measured to 2-3 min.

Tablet A2

Tablets A2 had a thickness of 5.65 to 5.68 mm. The disintegration time was measured to 18 seconds.

Dissolution

The % Cumulative Drug Release was measured in 900 ml 0.1 N HCl in a USP type II apparatus at 50 RPM for 30 minutes, with measurements performed at 5, 10, 20, and 30 minutes.

| 500 mg Nimorazole | % Cumulative Drug Release | | | |
|---|---|---|---|---|
| tablets | 5 min. | 10 min. | 20 min. | 30 min. |
| Tablet A1 | 74 | 94 | 96 | 100 |
| Tablet A2 | 86 | 94 | 96 | 98 |

The use of Crospovidone as a disintegrant instead of Sodium Starch Glycolate decreased the disintegration time, and provided a significant increase in dissolution rate, wherein more than 85% of the drug was released within 5 minutes.

Tablet A4

Preliminary experiments indicate Tablet A4 disintegrates in less than 3 minutes. About 85% of the active ingredient, Nimorazole, dissolves before 10 minutes, and the active ingredient is almost completely dissolved before 30 minutes.

The invention claimed is:

1. A solid pharmaceutical composition dosage form comprising:

i) nimorazole or a pharmaceutically acceptable salt thereof;

ii) a disintegrant;

iii) a coating sufficient to substantially mask the taste of nimorazole; and iv) optionally one or more additional excipients;

wherein said solid pharmaceutical composition dosage form allows administration both by directly swallowing the unaltered dosage form and by allowing the dosage form to disintegrate or disperse in an aqueous medium and to be administered to a patient via a feeding tube, and wherein one or more of said dosage forms are dispersible at a concentration of at least 1000 mg nimorazole in 100 ml water at 25° C. within 5 minutes upon stirring, thereby providing a dispersion that passes through a sieve screen with a nominal mesh aperture of 710 μm.

2. The solid pharmaceutical composition dosage form according to claim 1, wherein the additional excipients comprise a diluent, a binder, a glidant, and a lubricant.

3. The solid pharmaceutical composition dosage form according to claim 1, further comprising:

an intragranular part, comprising a diluent, a disintegrant, and a binder; and an extragranular part, comprising a diluent, a disintegrant, a glidant, and a lubricant.

4. The solid pharmaceutical composition dosage form according to claim 1, wherein said dosage form comprises at least 250 mg of nimorazole or a pharmaceutically acceptable salt thereof.

5. The solid pharmaceutical composition dosage form according to claim 1, wherein the dosage form is selected from the group consisting of a tablet and a sachet.

6. The solid pharmaceutical composition dosage form according to claim 1 that is formulated as an immediate release tablet or a dispersible tablet.

7. The solid pharmaceutical composition dosage form according to claim 1, wherein the pharmaceutical composition is manufactured by a process comprising a step of wet granulation, followed by a step of drying until a pre-determined loss on drying (% LOD) is obtained.

8. The solid pharmaceutical composition dosage form according to claim 1, wherein the pharmaceutical composition is manufactured by a process comprising a step of granulation and optionally a subsequent step of milling, such that essentially all granules are able to pass through a No. 20 sieve.

9. The solid pharmaceutical composition dosage form according to claim 1, for administration via a feeding tube, wherein the feeding tube is selected from the group consisting of a percutaneous endoscopic gastrostomy tube, a nasogastric feeding tube, a nasojejunal feeding tube, a gastric feeding tube, and a jejunostomy feeding tube.

10. The solid pharmaceutical composition dosage form according to claim 9, for administration via a percutaneous endoscopic gastrostomy tube or a nasogastric feeding tube.

11. The solid pharmaceutical composition dosage form according to claim 1, for treatment of cancer by radiosensitizing hypoxic tumor cells.

12. The solid pharmaceutical composition dosage form according to claim 1, for treatment of patients undergoing irradiation treatment.

13. The solid pharmaceutical composition dosage form according to claim 1, for treatment combined with chemotherapy.

14. The solid pharmaceutical composition dosage form according to claim 1, for treatment of an intubated patient.

15. The solid pharmaceutical composition dosage form according to claim 1, for curative treatment or reirradiation of cancer.

16. The solid pharmaceutical composition dosage form according to claim 1, for treatment of patients with hypoxic cancer.

17. The solid pharmaceutical composition dosage form according to claim 1, for treatment of an indication selected from the group consisting of breast cancer, head/neck cancer, lymphoma, cervical cancer, colorectal cancer, brain cancer, lung cancer, bladder cancer, and prostate cancer.

18. The solid pharmaceutical composition dosage form according to claim 17, for treatment of head/neck cancer.

19. The solid pharmaceutical composition dosage form according to claim 17, for treatment of cervical cancer or inoperable lung cancer.

20. The solid pharmaceutical composition dosage form according to claim 2, comprising:

diluent, 1-50 wt %;

disintegrant, 0.5-15 wt %;

binder, 0.5-15 wt %;

glidant, 0.5-3 wt %;

lubricant, 0.5-3 wt %;

optionally one or more additional excipients; and a coating, 0.5-5 wt %.

21. A kit of parts comprising the solid pharmaceutical composition dosage form according to claim 1, and instructions for preparing a dispersion of said dosage form for administration via a tube.

* * * * *